(12) United States Patent
Piskun

(10) Patent No.: US 11,241,560 B2
(45) Date of Patent: Feb. 8, 2022

(54) SYSTEM FOR A MINIMALLY-INVASIVE TREATMENT WITHIN A BODY LUMEN

(71) Applicant: Boston Scientific Scimed, Inc., Maple Grove, MN (US)

(72) Inventor: Gregory Piskun, Delray Beach, FL (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 374 days.

(21) Appl. No.: 15/917,152

(22) Filed: Mar. 9, 2018

(65) Prior Publication Data
US 2018/0264239 A1     Sep. 20, 2018

Related U.S. Application Data

(60) Provisional application No. 62/473,363, filed on Mar. 18, 2017.

(51) Int. Cl.
*A61M 25/10*      (2013.01)
*A61B 1/005*      (2006.01)
(Continued)

(52) U.S. Cl.
CPC ..... *A61M 25/10181* (2013.11); *A61B 1/0051* (2013.01); *A61B 1/00082* (2013.01);
(Continued)

(58) Field of Classification Search
CPC .. A61M 2025/1052; A61M 2025/1056; A61M 2025/105; A61M 25/10;
(Continued)

(56) References Cited

U.S. PATENT DOCUMENTS

| | | |
|---|---|---|
| 457,787 A | 8/1891 | Leisenring |
| 1,621,159 A | 3/1927 | Evans |

(Continued)

FOREIGN PATENT DOCUMENTS

| | | |
|---|---|---|
| CN | 201200436 Y | 3/2009 |
| CN | 102018493 A | 4/2011 |

(Continued)

OTHER PUBLICATIONS

"*Oleg Shikhman vs. Bobcat Endoscopy, LLC (F/K/A/ LumenR LLC) and Gregory Piskun, M.D.* Complaint", filed on Oct. 17, 2017, at Judicial District of Fairfield at Bridgeport, 25 pages.
(Continued)

*Primary Examiner* — Majid Jamialahmadi

(57) ABSTRACT

A system for endoscopic surgery within a body lumen of a patient including a flexible catheter having an expandable balloon at a distal portion and an access opening. The expandable balloon is expandable from a collapsed insertion configuration to an expanded configuration to provide an expanded chamber on a first side of the catheter. The access opening provides a window to access target tissue. The catheter includes a lumen dimensioned to receive an endoscopic instrument therethrough such that a distal end of the endoscopic instrument is positionable within the expanded chamber and angled laterally within the expanded chamber to access the target tissue through the window.

16 Claims, 8 Drawing Sheets

(51) Int. Cl.
  *A61M 25/00* (2006.01)
  *A61B 1/01* (2006.01)
  *A61B 1/00* (2006.01)
  *A61B 17/22* (2006.01)
  *A61B 90/00* (2016.01)
  *A61B 1/008* (2006.01)
  *A61B 17/00* (2006.01)
  *A61B 17/32* (2006.01)
  *A61B 17/29* (2006.01)
  *A61B 17/02* (2006.01)
  *A61B 90/40* (2016.01)

(52) U.S. Cl.
  CPC ............ *A61B 1/00135* (2013.01); *A61B 1/01* (2013.01); *A61B 17/22* (2013.01); *A61B 90/02* (2016.02); *A61M 25/10185* (2013.11); *A61B 1/008* (2013.01); *A61B 17/22031* (2013.01); *A61B 17/29* (2013.01); *A61B 17/320016* (2013.01); *A61B 90/40* (2016.02); *A61B 2017/00269* (2013.01); *A61B 2017/00557* (2013.01); *A61B 2017/00818* (2013.01); *A61B 2017/00867* (2013.01); *A61B 2017/0225* (2013.01); *A61B 2017/22068* (2013.01); *A61M 25/0026* (2013.01); *A61M 25/0068* (2013.01); *A61M 2025/1052* (2013.01)

(58) Field of Classification Search
  CPC .......... A61B 17/29; A61B 2017/22068; A61B 2017/22065; A61B 1/32; A61B 1/31; A61B 1/00082; A61B 1/0051; A61B 1/01
  See application file for complete search history.

(56) References Cited

U.S. PATENT DOCUMENTS

| | | |
|---|---|---|
| 3,517,128 A | 6/1970 | Hines |
| 4,040,413 A | 8/1977 | Ohshiro |
| 4,083,369 A | 4/1978 | Sinnreich |
| 4,224,929 A | 9/1980 | Furihata |
| 4,295,464 A | 10/1981 | Shihata |
| 4,519,403 A | 5/1985 | Dickhudt |
| 4,611,594 A | 9/1986 | Grayhack et al. |
| 4,966,596 A | 10/1990 | Kuntz et al. |
| 5,025,778 A | 6/1991 | Silverstein et al. |
| 5,059,199 A | 10/1991 | Okada et al. |
| 5,087,265 A | 2/1992 | Summers |
| 5,112,310 A | 5/1992 | Grobe |
| 5,197,971 A | 3/1993 | Bonutti |
| 5,386,817 A | 2/1995 | Jones |
| 5,411,508 A | 5/1995 | Bessler et al. |
| 5,423,830 A | 6/1995 | Schneebaum et al. |
| 5,655,698 A | 8/1997 | Yoon |
| 5,716,321 A | 2/1998 | Kerin et al. |
| 5,722,103 A | 3/1998 | Walega |
| 5,776,097 A | 7/1998 | Massoud |
| 5,840,031 A * | 11/1998 | Crowley ............ A61B 8/12 600/440 |
| 5,947,983 A | 9/1999 | Solar et al. |
| 5,954,731 A | 9/1999 | Yoon |
| 5,997,547 A | 12/1999 | Nakao et al. |
| 6,009,877 A | 1/2000 | Edwards |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,203,552 B1 | 3/2001 | Bagley et al. |
| 6,214,024 B1 | 4/2001 | Houser |
| 6,264,086 B1 | 7/2001 | McGuckin, Jr. |
| 6,302,311 B1 | 10/2001 | Adams et al. |
| 6,343,731 B1 | 2/2002 | Adams et al. |
| 6,405,732 B1 | 6/2002 | Edwards et al. |
| 6,423,058 B1 | 7/2002 | Edwards et al. |
| 6,428,473 B1 | 8/2002 | Leonard et al. |
| 6,494,881 B1 | 12/2002 | Bales et al. |
| 6,616,603 B1 | 9/2003 | Fontana |
| 6,695,198 B2 | 2/2004 | Adams et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams |
| 7,059,331 B2 | 6/2006 | Adams et al. |
| 7,169,115 B2 | 1/2007 | Nobis et al. |
| 7,276,066 B2 | 10/2007 | Ouchi |
| 7,396,329 B2 | 7/2008 | Nakao |
| 7,445,598 B2 | 11/2008 | Orban, III |
| 7,918,787 B2 | 4/2011 | Saadat |
| 7,959,559 B2 | 6/2011 | Yamaya |
| 8,007,508 B2 | 8/2011 | Cox |
| 8,088,139 B2 | 1/2012 | Scopton et al. |
| 8,277,373 B2 | 10/2012 | Maahs et al. |
| 8,506,479 B2 | 8/2013 | Piskun et al. |
| 8,517,933 B2 | 8/2013 | Mohr |
| 8,608,652 B2 | 12/2013 | Voegele et al. |
| 8,764,630 B2 | 7/2014 | Yamatani |
| 8,764,785 B2 | 7/2014 | Scopton et al. |
| 8,777,961 B2 | 7/2014 | Cabrera et al. |
| 8,932,326 B2 | 1/2015 | Riina et al. |
| 8,979,884 B2 | 3/2015 | Milsom et al. |
| 9,050,004 B2 | 6/2015 | Diao et al. |
| 9,161,746 B2 | 10/2015 | Piskun et al. |
| 9,168,053 B2 | 10/2015 | Cox |
| 9,259,233 B2 | 2/2016 | Gruber et al. |
| 9,370,379 B2 | 6/2016 | Osman |
| 9,375,224 B2 | 6/2016 | Jansen |
| 9,661,984 B2 | 5/2017 | Piskun |
| 2001/0004947 A1 | 6/2001 | Lemke et al. |
| 2001/0047169 A1 | 11/2001 | McGuckin, Jr. et al. |
| 2001/0049497 A1 | 12/2001 | Kalloo et al. |
| 2002/0123748 A1 | 9/2002 | Edwards et al. |
| 2002/0177870 A1 * | 11/2002 | Sepetka ............ A61M 25/10 606/194 |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0050663 A1 | 3/2003 | Khachin et al. |
| 2003/0074015 A1 | 4/2003 | Nakao |
| 2003/0135230 A1 | 7/2003 | Massey et al. |
| 2003/0225432 A1 | 12/2003 | Baptiste et al. |
| 2003/0225433 A1 | 12/2003 | Nakao |
| 2004/0034278 A1 | 2/2004 | Adams |
| 2004/0082859 A1 | 4/2004 | Schaer |
| 2004/0158263 A1 | 8/2004 | McAlister et al. |
| 2004/0204725 A1 | 10/2004 | Bayer |
| 2005/0177105 A1 | 8/2005 | Shalev |
| 2005/0234297 A1 | 10/2005 | Devierre et al. |
| 2005/0234299 A1 | 10/2005 | Eitenmuller et al. |
| 2005/0240147 A1 | 10/2005 | Makower et al. |
| 2005/0251111 A1 | 11/2005 | Saito et al. |
| 2005/0251177 A1 | 11/2005 | Saadat et al. |
| 2005/0272977 A1 | 12/2005 | Saadat et al. |
| 2006/0074277 A1 | 4/2006 | Yoshida |
| 2006/0100480 A1 | 5/2006 | Ewers et al. |
| 2006/0189845 A1 | 8/2006 | Maahs et al. |
| 2006/0191975 A1 | 8/2006 | Adams et al. |
| 2006/0247662 A1 | 11/2006 | Schwartz et al. |
| 2006/0264706 A1 | 11/2006 | Piskun |
| 2007/0005093 A1 | 1/2007 | Cox |
| 2007/0021778 A1 | 1/2007 | Carly |
| 2007/0255207 A1 | 11/2007 | Hangai et al. |
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyama et al. |
| 2008/0103479 A1 * | 5/2008 | Cheng ............ A61B 17/1214 604/510 |

(56) References Cited

U.S. PATENT DOCUMENTS

| | | | |
|---|---|---|---|
| 2008/0132835 | A1 | 6/2008 | Nagamatsu et al. |
| 2008/0161645 | A1 | 7/2008 | Goldwasser et al. |
| 2008/0188868 | A1 | 8/2008 | Weitzner et al. |
| 2008/0228209 | A1 | 9/2008 | DeMello et al. |
| 2008/0249534 | A1 | 10/2008 | Gruber et al. |
| 2008/0269557 | A1 | 10/2008 | Marescaux et al. |
| 2008/0269559 | A1 | 10/2008 | Miyamoto et al. |
| 2008/0275300 | A1 | 11/2008 | Rothe et al. |
| 2008/0300454 | A1 | 12/2008 | Goto |
| 2009/0018500 | A1 | 1/2009 | Carter et al. |
| 2009/0030369 | A1 | 1/2009 | Nagamatsu et al. |
| 2009/0149716 | A1 | 6/2009 | Diao et al. |
| 2009/0156996 | A1 | 6/2009 | Milsom et al. |
| 2009/0287046 | A1 | 11/2009 | Yamatani |
| 2009/0312645 | A1 | 12/2009 | Weitzner et al. |
| 2010/0010296 | A1 | 1/2010 | Piskun |
| 2010/0049137 | A1 | 2/2010 | Fischer, Jr. |
| 2010/0106240 | A1 | 4/2010 | Duggal et al. |
| 2010/0152590 | A1 | 6/2010 | Moore et al. |
| 2011/0065985 | A1 | 3/2011 | Wehrheim |
| 2011/0077498 | A1 | 3/2011 | McDaniel |
| 2011/0160538 | A1 | 6/2011 | Ravikumar et al. |
| 2011/0172491 | A1 | 7/2011 | Piskun et al. |
| 2011/0224494 | A1 | 9/2011 | Piskun et al. |
| 2011/0245858 | A1 | 10/2011 | Milsom et al. |
| 2011/0306832 | A1 | 12/2011 | Bassan et al. |
| 2012/0083797 | A1 | 4/2012 | Cabrera et al. |
| 2012/0095498 | A1 | 4/2012 | Stefanchik et al. |
| 2012/0109178 | A1 | 5/2012 | Edwards et al. |
| 2012/0165604 | A1 | 6/2012 | Stokes et al. |
| 2013/0090527 | A1 | 4/2013 | Axon |
| 2013/0172828 | A1 | 7/2013 | Kappel et al. |
| 2013/0274553 | A1 | 10/2013 | Piskun et al. |
| 2013/0317303 | A1 | 11/2013 | Deshmukh et al. |
| 2013/0324795 | A1 | 12/2013 | Nakajima et al. |
| 2014/0316379 | A1 | 10/2014 | Sonderegger et al. |
| 2015/0150436 | A1 | 6/2015 | Cornhill et al. |
| 2015/0157192 | A1 | 6/2015 | Piskun et al. |
| 2015/0265268 | A1 | 9/2015 | Diao et al. |
| 2015/0265818 | A1 | 9/2015 | Piskun et al. |
| 2015/0272564 | A1 | 10/2015 | Piskun et al. |
| 2015/0351890 | A1 | 12/2015 | Levin et al. |
| 2016/0038172 | A1 | 2/2016 | Cox |
| 2016/0081702 | A1 | 3/2016 | Kan et al. |
| 2016/0106466 | A1 | 4/2016 | Gruber et al. |
| 2016/0157843 | A1 | 6/2016 | Dickson et al. |
| 2016/0374658 | A1 | 12/2016 | Piskun |

FOREIGN PATENT DOCUMENTS

| | | |
|---|---|---|
| CN | 102695541 A | 9/2012 |
| EP | 0163502 A2 | 12/1985 |
| EP | 1588670 A1 | 10/2005 |
| EP | 2512577 A2 | 10/2012 |
| GB | 2365340 A | 2/2002 |
| JP | S63292935 A | 11/1988 |
| JP | H08317928 A | 12/1996 |
| JP | H08336538 A | 12/1996 |
| JP | 2533732 Y2 | 4/1997 |
| JP | H09503677 A | 4/1997 |
| JP | H1028691 A | 2/1998 |
| JP | 2000166936 A | 6/2000 |
| JP | 2000325303 A | 11/2000 |
| JP | 2001527429 A | 12/2001 |
| JP | 2003522590 A | 7/2003 |
| JP | 2004154485 A | 6/2004 |
| JP | 2004529708 A | 9/2004 |
| JP | 2005046274 A | 2/2005 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 A | 4/2012 |
| JP | 2013514827 A | 5/2013 |
| JP | 2015000280 A | 1/2015 |
| JP | 2015525109 A | 9/2015 |
| WO | 9101773 A1 | 2/1991 |
| WO | 9635469 A1 | 11/1996 |
| WO | 9640347 A1 | 12/1996 |
| WO | 03000139 A1 | 1/2003 |
| WO | 2004103430 A2 | 12/2004 |
| WO | 2006110275 A2 | 10/2006 |
| WO | 2007081601 A2 | 7/2007 |
| WO | 2008011163 A2 | 1/2008 |
| WO | 2009059296 A1 | 5/2009 |
| WO | 2009076176 A1 | 6/2009 |
| WO | 2009117696 A1 | 9/2009 |
| WO | 2011084616 A2 | 7/2011 |
| WO | 2012068048 A1 | 5/2012 |
| WO | 2012114569 A1 | 8/2012 |
| WO | 2013050880 A2 | 4/2013 |
| WO | 2013192116 A1 | 12/2013 |
| WO | 2014200737 A1 | 12/2014 |
| WO | 2015026968 A1 | 2/2015 |
| WO | 2015191125 A1 | 12/2015 |

OTHER PUBLICATIONS

"*Oleg Shikhman* vs. *Bobcat Endoscopy, LLC (F/K/A/ LumenR LLC) and Gregory Piskun, M.D*. Reply to Affirmative Defenses, Matters in Avoidance and Answer to Counterclaims", dated Dec. 12, 2018, 19 pages.

"*Oleg Shikhman* vs. *Bobcat Endoscopy, LLC (F/K/A/ LumenR LLC) and Gregory Piskun, M.D.*, Answer, Special Defenses and Counterclaims", dated September. 13, 2018, 23 pages.

"*Oleg Shikhman* vs. *Bobcat Endoscopy, LLC (F/K/A/ LumenR LLC) and Gregory Piskun, M.D.*, First Amended Answer, Affirmative Defenses and Counterclaims", dated Nov. 9, 2018, 24 pages.

"Letter from Jeffrey M. Chamberlain, Senior Principal at Kacvinsky Daisak Bluni pllc to Michael J. Rye, Esq, c/o Cantor Colburn, LLP", dated Nov. 13, 2018, 3 pages.

"Letter from Michael J. Rye, Partner at Cantor Colburn LLP to Michael Mahoney, CEO at Boston Scientific Corporation", dated Oct. 17, 2017, 3 pages.

Letter from Michael J. Rye, Partner at Cantor Colburn LLP to Jeffrey M. Chamberlain at Kacvinsky Daisak Bluni PLLC, dated Aug. 28, 2018, 2 pages.

International Search Report and Written Opinion for International Application No. PCT/US2016/016911, dated May 6, 2016, 9 pages.

International Search Report and Written Opinion for application No. PCT/US2014/040429, dated Aug. 1, 2014, 11 pages.

European Search Report dated Apr. 7, 2011 for European Patent Application No. 06789411.3, 5 pages.

Written Opinion for International Application No. PCT/US06/30464, dated Jun. 20, 2007, 5 pages.

Communication for European Patent Application No. 14733912.1, dated Jun. 11, 2018, 2 pages.

International Search Report and Written Opinion for International Application No. PCT/US18/21779, dated Jun. 14, 2018, 10 pages.

International Search Report and Written Opinion (dated Dec. 14, 2017), for PCT/US2017/050685 (16 pages).

International Search Report and Written Opinion for PCT/US10/60802, dated Aug. 24, 2011, 12 pages.

International Search Report and Written Opinion for International Application No. PCT/US2016/031355, dated Sep. 23, 2016, 17 pages.

International Search Report and Written Opinion for International Application No. PCT/US18/14388, dated Jun. 19, 2018, 9 pages.

"*Sergey Kantsevoy* vs. *LumenR LLC*, Answer, Affirmative Defenses and Counterclaims", Civil Action No. 17-cv-359 (ELH), filed Feb. 28, 2017, 25 pages.

"Letter from Kurt W. Lockwood, Principal at Kacvinsky Daisak Bluni pllc, to Philip G. Hampton, II c/o Haynes and Boone, LLP" dated Nov. 9, 2018, 16 pages.

(56) References Cited

OTHER PUBLICATIONS

"Letter from Philip G. Hampton, II at Haynes and Boone, LLP to Kurt W. Lockwood, Esq. at Kacvinsky Daisak Bluni PLLC", dated Nov. 16, 2018, 2 pages.

"*Sergey Kantsevoy* v. *LumenR LLC* Complaint, Civil Action No. 17-359", filed Feb. 7, 2017, 18 pages.

"*Sergey Kantsevoy* v. *LumenR LLC*, Dr. Sergey Kantsevoy's Answer to LumenR LLC's Counterclaims", Civil Action No. 17-359 (ELH), filed Mar. 17, 2017, 8 pages.

\* cited by examiner

SYSTEM FOR A MINIMALLY-INVASIVE TREATMENT WITHIN A BODY LUMEN

CROSS-REFERENCE TO RELATED APPLICATIONS

This application claims the benefit of priority under 35 U.S.C. § 119 to U.S. Provisional Application Ser. No. 62/473,363, filed Mar. 18, 2017, the disclosure of which is herein incorporated herein by reference in its entirety.

BACKGROUND

This application relates to minimally invasive devices for operatively treating tissue and more specifically to minimally invasive devices which expand and/or reshape the body lumen to increase and/or optimize the working space to enable or enhance maneuverability of endoscopic instruments.

Endoscopic procedures involving the gastrointestinal system offer advantages over conventional surgery in that they are typically less invasive and may provide or improve visualization.

It may be advantageous to provide a stable, optimal working (operating) space to expand and/or reconfigure (reshape) the working space during a minimally invasive (endoscopic) procedure. Such stable, expanded and/or optimally configured working space facilitates independent manipulation of the instruments and endoscope and improves endoscopic visualization of the target tissues.

It may also be advantageous to provide endoscopic technology for organizing the endoscope, instruments, and working space in a manner that can maximize the working space for treatment. The larger working space can improve the ability to manipulate the instruments and endoscope in a minimally-invasive manner from outside the body. It is advantageous to have a working space that has tips of the instruments as far as practical from the target tissue to improve the maneuverability of the instruments and provide additional flexibility in approaching and visualizing the target tissue, perhaps providing more operating room for selecting a trajectory of the instruments toward the target tissue that is, for example, at least substantially perpendicular or substantially parallel to the plane of dissection of the target tissue.

SUMMARY

The systems disclosed herein provide improved methods and devices for minimally invasively treating tissue, such as gastrointestinal tissue. The systems, for example, include a reversibly-expandable member or retractor that expands, preferably in an asymmetric manner, to maximize space for endoscopic tools(s), and in some embodiments an endoscope, to each be maneuvered independently from outside the patient to visualize a target tissue and treat the target tissue in a minimally invasive manner. Embodiments taught herein provide an increase in distance between tool ports/tools and the target tissue to improve maneuverability and triangulation of the tools with respect to the target tissue, as well as a larger field of view.

In one aspect, the present disclosure relates to a system for endoscopic surgery within a body lumen of a patient comprising a flexible catheter having a proximal portion, a distal portion, and an expandable balloon at the distal portion. The expandable balloon may include a side access opening. The expandable balloon may be inflatable/expandable to expand from a collapsed insertion configuration to an expanded configuration. The expandable balloon may expand asymmetrically and have an increased transverse dimension to provide an expanded chamber on a first side of the catheter. The access opening may be positioned on the first side of the catheter to provide a side window to access target tissue. The catheter may include a lumen dimensioned to receive an endoscopic instrument therethrough, such that a distal end of the endoscopic instrument may be positionable within the expanded chamber and may be angled laterally within the expanded chamber to access the target tissue through the window. The lumen of the catheter may include an opening at a distal end communicating with the chamber. The catheter may be dimensioned to receive a visualization device to visualize the target tissue. The endoscopic instrument may be received in the lumen of the catheter, and may be movable independently of the visualization device. The catheter may include an inflation channel for expanding the balloon. The expandable balloon may be generally uniform in transverse dimension along its length. The expandable balloon may be C-shaped in transverse cross-section. The system may further comprise an articulation member for angling the distal portion of the catheter with respect to a longitudinal axis of the catheter. The expandable balloon may form the terminal end of the chamber. The expandable balloon may have a U-shape forming a space or opening within the U. The endoscopic instrument may have a first curve extending in a first direction, and a second curve extending in an opposite direction. The first curve may angle away from the window and the second curve may angle toward the window. The catheter may have a seal at a distal end, and the visualization device may be movable through the seal to visualize distally of the catheter. The system may further comprise a flexible guide positionable within the lumen of the catheter. The flexible guide may have a distal portion extendable into the expandable chamber, and the endoscopic instrument may be insertable through the flexible guide. An intermediate portion of the expandable member may have a transverse dimension greater than a proximal portion and a distal portion, and the side window may be located in the intermediate portion. The system may further include the visualization device with a distal end positioned adjacent a proximal region of the expanded chamber. The catheter may have a seal at a distal end, and the visualization device may be movable through the seal to visualize distally of the catheter.

In another aspect, the present disclosure relates to a flexible catheter for endoscopic surgery within a body lumen of a patient comprising a proximal portion and a distal portion having an expandable balloon expandable from a collapsed insertion configuration to an expanded configuration. The expandable balloon may expand asymmetrically and may have an increased transverse dimension to provide an expanded chamber on a first side of the catheter. The balloon may have a U-shape with a space within the U forming an opening to provide access to target tissue. The catheter may include a lumen having a distal opening communicating with the expanded chamber. The expandable balloon may have an intermediate portion with a transverse dimension greater than a proximal portion and a distal portion, and the space may be located in the intermediate portion. The expandable balloon may form the terminal end of the chamber. The catheter may include a seal at its distalmost end. The catheter may have first and second lumens to receive first and second tool channels.

In yet another aspect, the present disclosure relates to a method of minimally invasively treating tissue comprising, inserting into a body lumen of a patient an endoscopic device having an expandable balloon in a collapsed configuration. The expandable balloon may have a side access opening. After insertion of the endoscopic device into the body lumen (of the patient), the method may further include expanding the balloon from the collapsed configuration to an expanded configuration to create a chamber of increased transverse dimension to increase a distance between a longitudinal axis and the side access opening. The method may further include inserting a distal portion of a working instrument into the chamber. The working instrument may extend through a first channel in the endoscopic device, and the distal portion of the working instrument may extend laterally with respect to the longitudinal axis of the endoscopic device. The working instrument accessing the target tissue may protrude through the window or access the target tissue by extending through the window. The method may further include visualizing the distal portion of the working instrument by a visualization device. The step of expanding the balloon may expand the chamber to only one side of the longitudinal axis of the endoscopic device/instrument, and may retract tissue adjacent the target tissue. The method may further include inserting a tool channel into the first channel of the endoscopic device. The working instrument may be inserted through the tool channel. The tool channel may have a curved portion extending toward the target issue when exposed from the endoscopic device.

DETAILED DESCRIPTION

Figure 1:
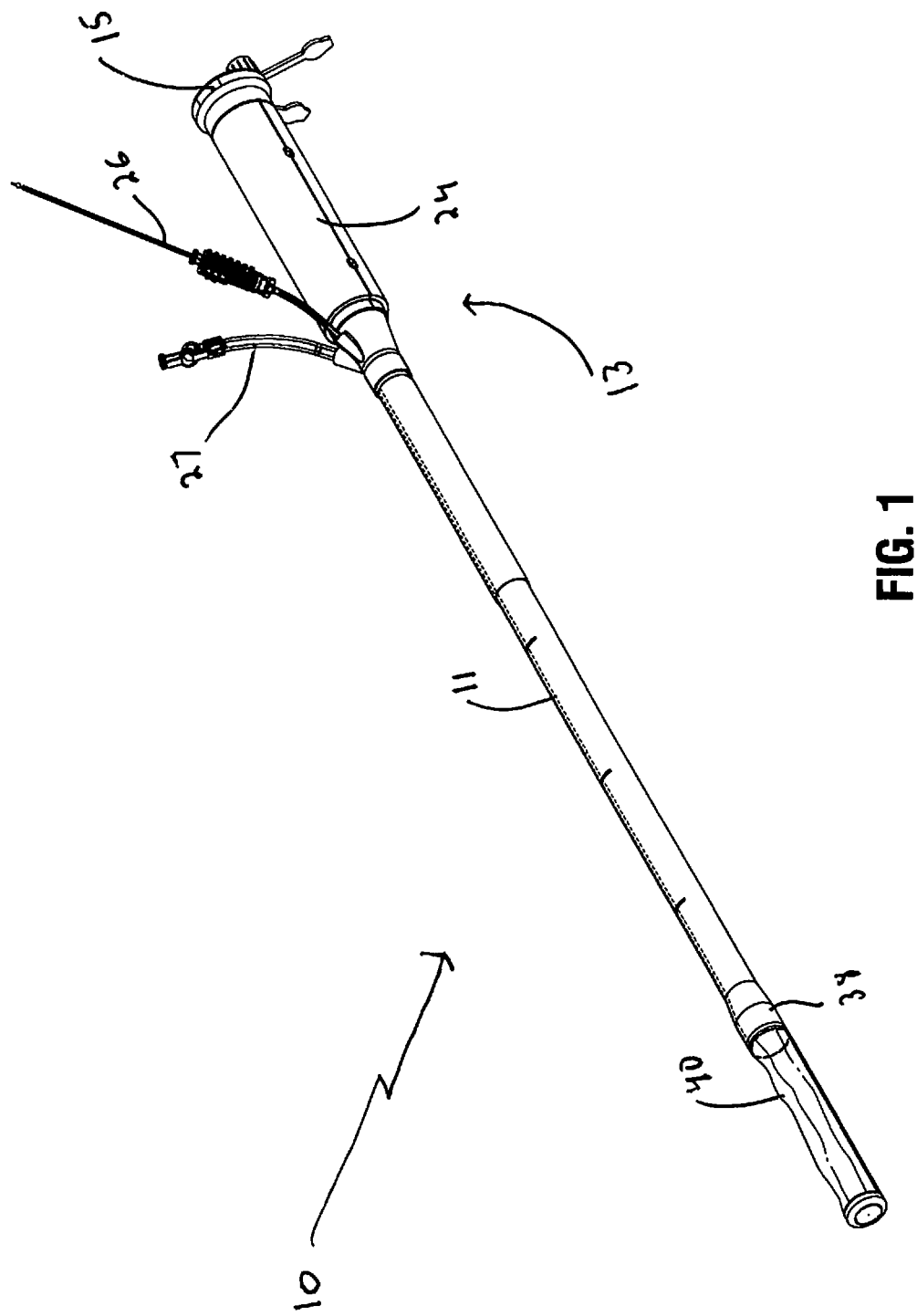
FIG. 1 is a perspective view of a first embodiment of the system of the present disclosure showing the balloon of the catheter in the non-expanded insertion position.

The disclosure is directed to improved systems, methods and devices for operatively treating disorders, such as gastrointestinal disorders, in a minimally-invasive manner. The systems can include an expandable portion that expands, preferably asymmetrically to maximize space for endoscopic tools, and an endoscope to each be maneuvered from outside the patient independently to visualize a target tissue and treat the target tissue in a minimally invasive manner. The systems include a side window (access opening) within the expandable portion or expandable member to provide access to the target tissue. Expansion of the expandable member moves the wall of the body lumen further away from longitudinal axis of the catheter to increase the working space. The systems disclosed herein advantageously increase a distance between tips of the endoscopic tools (instruments) and the target tissue to enhance the independent maneuverability and triangulation of the tools with respect to the target tissue. This increase in distance can also provide a way of obtaining a larger field of view. The systems taught herein, for example, can (i) enable a working space to be dynamically configured in tortuous body lumens and orifices such as the gastrointestinal tract using controls from outside the body; (ii) provide a flexible passageway for multiple surgical tools and instruments, such as an endoscope and endoscopic tools, for example, tissue manipulating tools such as graspers and/or tissue cutting devices with or without energy, to be passed from outside the body towards the target tissue; (iii) organize and/or constrain tools in the working space; (iv) at least substantially immobilize and/or stabilize tissue; and/or (v) enable control over the position and orientation of the instruments such as the grasper or tissue dissector (scissors, energy-based cutting device, etc.) in the working space from outside the body.

In some embodiments, an articulating endoscope is inserted through a channel of the catheter; in other embodiments the system is backloaded over a flexible endoscope, such as a conventional colonoscope, then the endoscope is inserted to a position adjacent the target tissue and then the catheter is advanced over the flexible endoscope so the expandable portion of the catheter is aligned with or adjacent the target tissue.

In some embodiments, the endoscopic working instruments (tools) for treating the target tissue are inserted directly through a respective lumen or channel of the multi-lumen catheter. In these embodiments, the working instruments can have a curve or double curve at a distal end which automatically assumes the curved position when exposed from the catheter, or alternatively, the working instruments can have a mechanism actively controlled by the user to articulate/angle the distal tip to form the curved or double curved shape. The single curved instrument can curve toward the window when exposed from the catheter; the double curved instrument can initially curve away from the target tissue, e.g., away from the access window, and then curve back toward the window (opening) and target tissue. In other embodiments, instead of the endoscopic working instruments (tools) being inserted directly into the lumen or channel of the catheter, a flexible tube (also referred to herein as a flexible guide or tool channel) is inserted through the lumen or channel of the catheter and acts as a guide for the endoscopic working instrument. That is, the flexible guide (tool channel) is first inserted into the lumen or channel of the catheter and then the endoscopic working instrument is inserted through the respective flexible guide. The flexible guides (tubes) can have a single curve or double curve at a distal end which automatically assumes the curved position when exposed from the catheter. The single curved flexible guide can curve toward the window when exposed from the catheter; the double curved flexible guide can initially curve away from the target tissue, e.g., away from the access window, and then curve back toward the window (opening) and target tissue. Alternatively, the flexible tubes can have a mechanism actively controlled by the user to articulate/angle the distal tip of the flexible tubes to form the curved or double curved shape. In these embodiments utilizing the flexible tubes, the curving and maneuverability of the flexible tubes controls the positioning and orientation of the endoscopic instruments, and therefore the endoscopic instruments need not be provided with a pre-curved tip or bending mechanisms, although optionally they can have a pre-bent (pre-curved) tip. The tool channels can be substantially straight when in the insertion position within the confines of the multi-lumen tube (catheter) and return to the pre-bent position when exposed from the confines of the catheter. In other embodiments, the tool channels terminate at the distal opening of the catheter and the working instruments have the curved tips.

In preferred embodiments, the systems disclosed herein include an expandable portion (region) or member which creates an expanded working space within the body lumen. More particularly, when working in a confined body lumen, such as the colon, expansion of the lumen is limited because it is undesirable to over-expand which could stretch the lumen beyond its ability to return to its normal state or more dangerously could rupture the lumen. The asymmetric working spaces disclosed herein are designed to expand, reconfigure and/or reshape the body lumen—transform the cylindrical space within the body lumen to a non-cylindrical asymmetrical space (i.e., change the geometry) to shift the space to create more working space and distance for instrument access to the target tissue to provide both visual and mechanical improvements. Stated another way, in a cylindrical working space, there is a lot of area of unused space while in the reshaping embodiments disclosed herein, the space is moved or shifted to reduce the unused space and create a larger area for tissue access and treatment.

The systems disclosed herein also enable triangulation of the scope and the instruments to be achieved. The triangulation, when the scope and the instrument(s) can form a triangle, enhances the instrument maneuverability and manipulation of the target tissue.

The systems disclosed herein also create a substantially enclosed chamber for withdrawal of tissue.

The tools inserted directly through the catheter lumen or through the flexible guide can be any type of endoscopic tool including for example, a grasper, a forceps, a snare, a scissor, a knife, a dissector, a clamp, an endoscopic stapler, a tissue loop, a clip applier, a suture-delivering instrument, or an energy-based tissue coagulator or cutter.

Although two tool channels are illustrated, it should also be appreciated that a system with more than two tool channels or with only one tool channel can also be utilized. Additionally, the endoscope can have a working channel for insertion of one or more working instruments such as a grasper or dissector. The endoscope is shown in use as terminating adjacent the opening in the catheter at a proximal end of the expanded chamber formed by the expandable member, however, it is also contemplated that the endoscope can be inserted into the chamber and manipulated and/or articulated within and outside the chamber.

In addition to creating the working space with the above advantages, the working space is formed to create an increased working distance for the tools for treatment, e.g., polyp dissection, to enhance maneuvering and manipulating the individual tools, and enabling instrument triangulation. Working space distance is also advantageously increased to enhance visibility of the target tissue.

This increased maneuverability can improve the view of the lesion and ability to manipulate and dissect the lesion. For example, a grasper can be advanced out of the instrument channel into the working space and flexed towards the polyp, then actuated to grasp the polyp and retract the tissue to expose the base of the polyp for dissection by a dissection tool through the multi-channel systems taught herein.

The systems provided herein can be used in several different methods of treatment. For example, the systems can be used in a method of treating a gastrointestinal lesion. The lesion can include, for example, a perforation, a tissue pathology a polyp, a tumor, a cancerous tissue, a bleed, a diverticuli, an ulcer, an abnormal vessel, or an appendix.

The expandable member in some embodiments is closable to capture and isolate the removed target tissue during removal of the catheter from the subject. This is advantageous if the dissected tissue may be a cancerous or it is otherwise desirable to contain it during removal of the catheter from the body lumen.

Figure 4A:
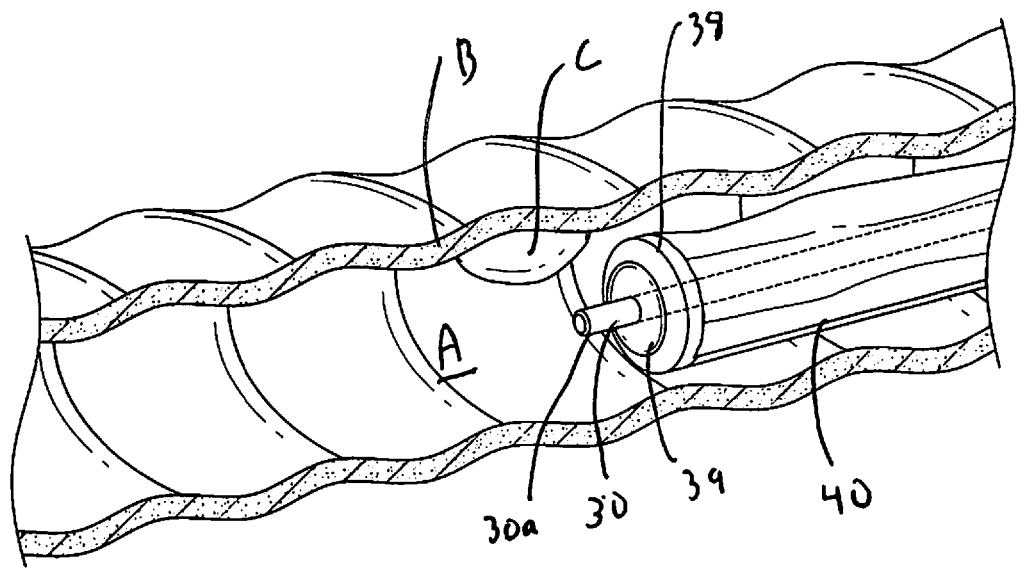
FIG. 4A is a perspective view showing the catheter of FIG. 1 inserted into the body lumen.

Turning now to the drawings, wherein like reference numerals identify the same parts or components, FIG. 1 illustrates a first embodiment of the system, designated generally by reference numeral 10. System 10 includes a flexible catheter or tubular member 11 configured to receive one or more tool channels or flexible instrument guides. FIG. 4C shows two tool channels 12, 14, it being understood that in some embodiments, only one tool channel can be utilized and in other embodiments more than two tool channels can be utilized. The catheter 11 can have multiple lumens to receive the tool channels. The tool channels 12, 14 can be packaged as a kit with the catheter 11 or alternatively, the tool channels 12, 14 can be packaged separately. In other embodiments, the tool channels are packaged already inside the lumens of the catheter 11. Each tool channel 12, 14 has a lumen (channel) extending from a proximal to a distal end to receive an endoscopic instrument (tool) therethrough. Note in alternate embodiments, the endoscopic instruments can be inserted directly through the catheter instead of through tool channels, as discussed in more detail below.

Figure 5C:
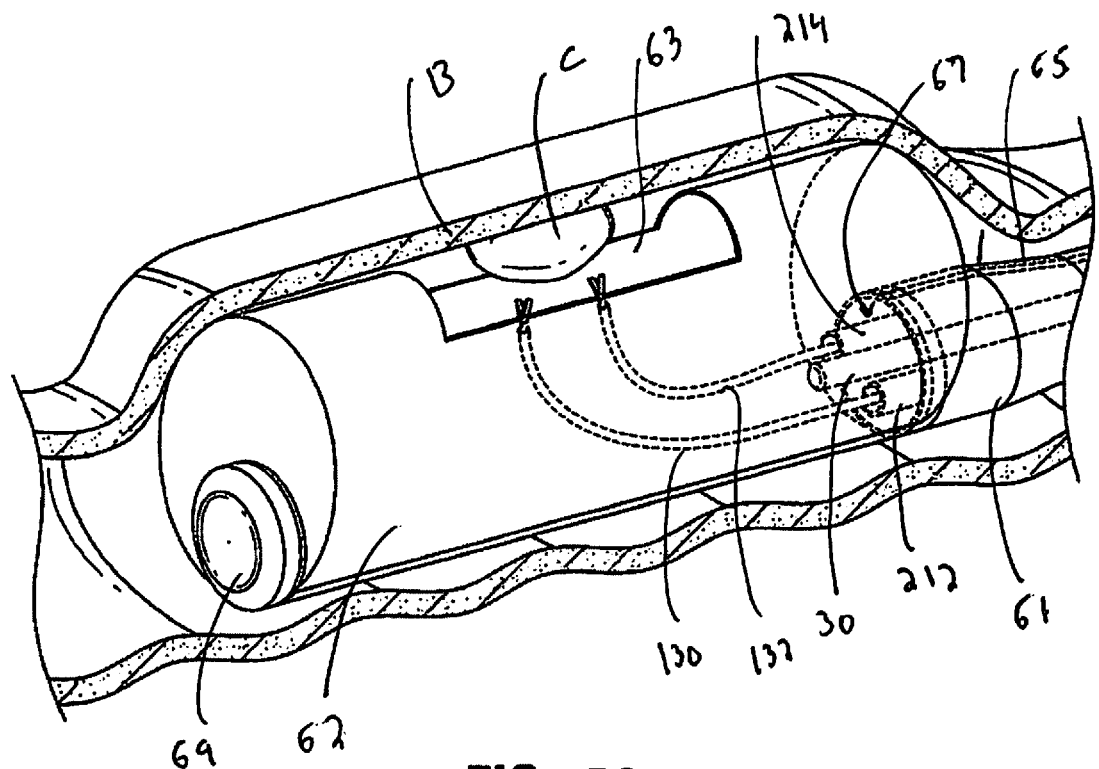
FIG. 5C is a perspective view showing the catheter of FIG. 5A inserted into the body lumen with the balloon expanded to provide an expanded chamber and further showing tool channels (instrument guides) and endoscopic tools (instruments) inserted through the tool channels.
Figure 5D:
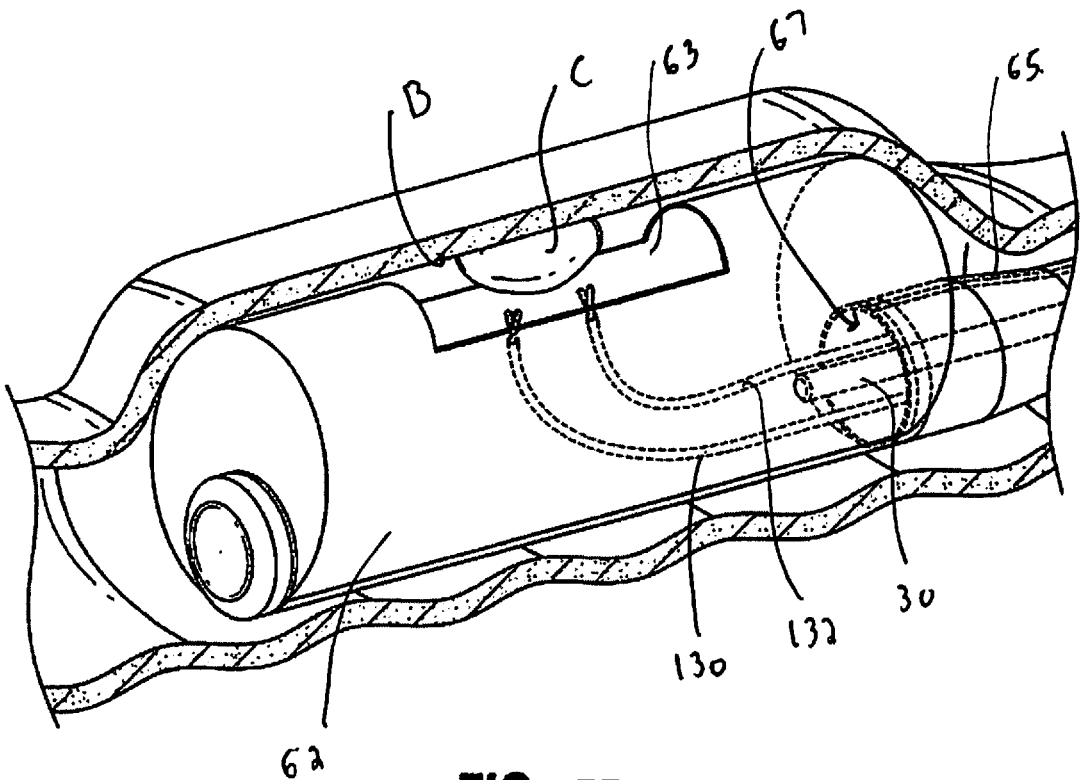
FIG. 5D is a view similar to FIG. 5C showing an alternate embodiment wherein the endoscopic tools are inserted through the catheter without the use of tool channels.
Figure 6:
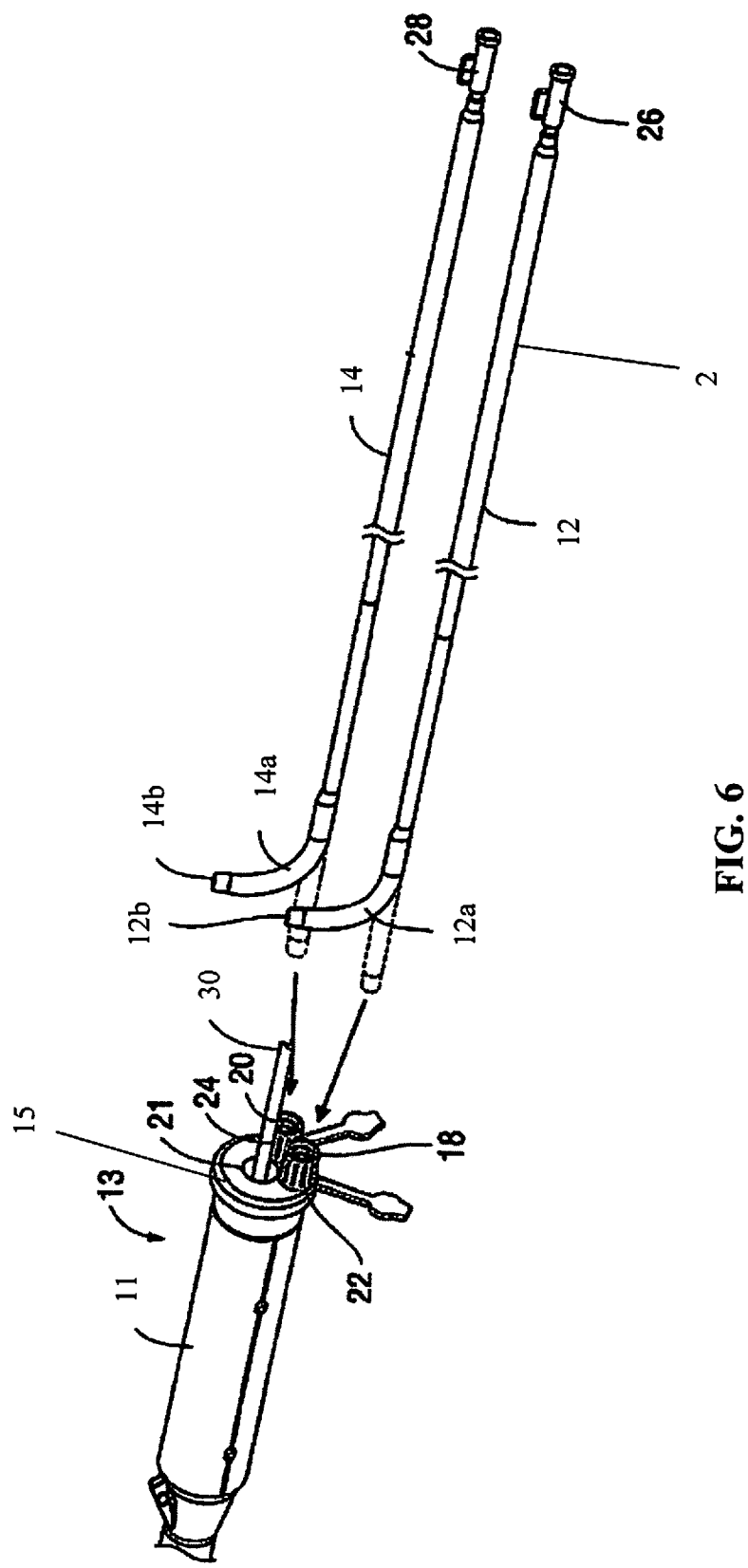
FIG. 6 is a perspective view of one embodiment of the tool channels.

The tool channels 12, 14 (also referred to herein as flexible tubes or flexible guides) are inserted through the proximal end 15 of the catheter 11 and advanced through respective lumens in the catheter 11. The lumens provide communication with the expanded chamber of the catheter and have distal openings proximate the chamber. The catheter 11 can include ports 22, 24 at a proximal end, cooperating with the tool channels 12, 14, which can include valves to maintain insufflation when the tool channels 12, 14 are inserted therethrough and translated axially therein. The tool channels 12, 14 can have a pre-bent curve as shown for example in the embodiment in FIG. 4C, the tool channels 12, 14 extending beyond distal opening 18, or the tool channels can be of shorter length and terminate at the opening 18 of catheter 11 as in tool channels 212, 214 of FIG. 5C. FIG. 6 illustrates these single curve tool channels 12, 14, with curved tips 12b, 14b, respectively, through which to instruments (tools) extend.

Figure 7:
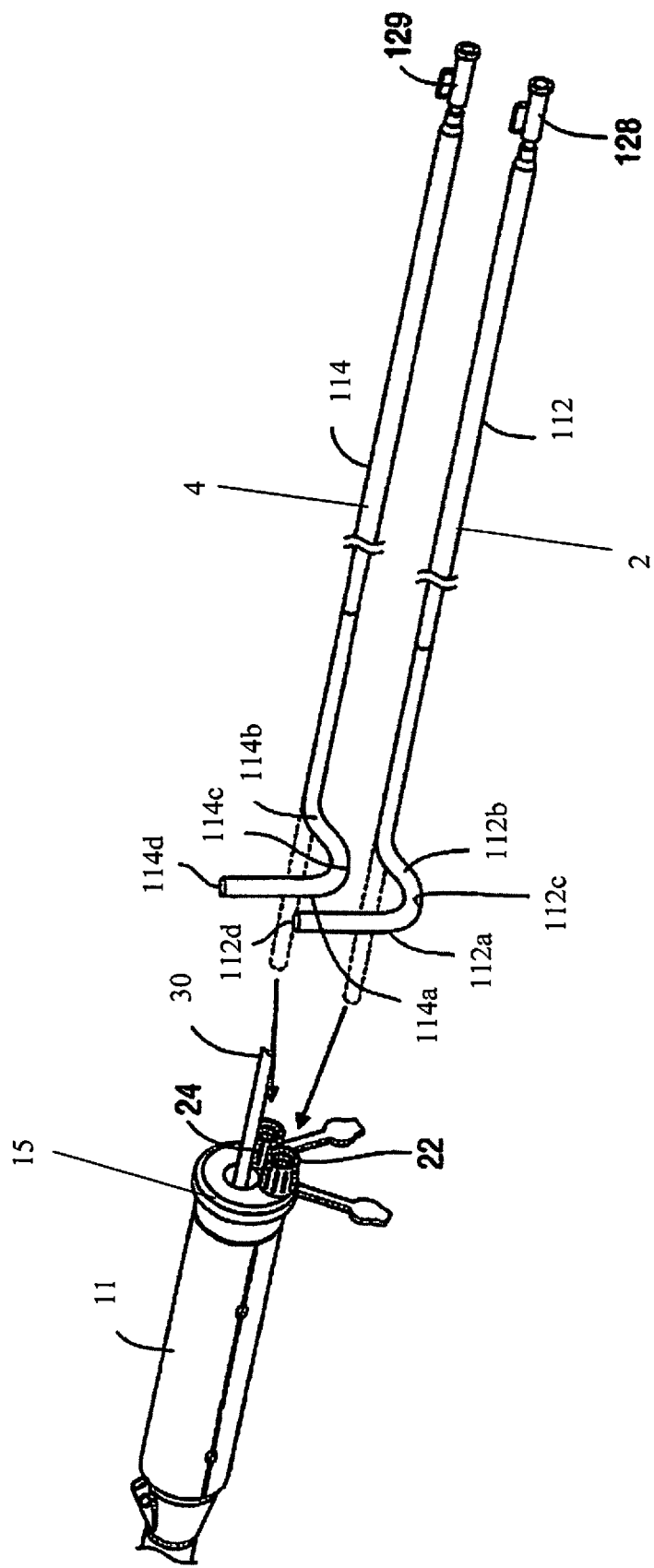
FIG. 7 is a perspective view of an alternate embodiment of the tool channels having a double curve.

In the alternate embodiment of FIG. 7, tool channel (tube) 112 has a pre-bent tip 112a to provide a double curved distal end. The pre-bend preferably takes the form of a first bend 112b extending away from the target tissue (and opening 45 in the expandable member 40) and transitioning to a second bend 112c extending downwardly toward the target tissue. Tool channel (tube) 114 also preferably has a pre-bent tip 114a, providing a curved distal end. The pre-bend preferably takes the form of a first bend 114b extending away from the target tissue (and opening 45 in the expandable member 40) and transitioning to a second bend 114c extending downwardly toward the target tissue. When the tool channels 112, 114 are inserted into the lumens of catheter 111, the tips 112a, 114a are preferably substantially straightened to facilitate advancement through the lumens. When the tool channels 112, 114 are advanced sufficiently distally so the distal tips 112a, 114a are exposed from the confines of the walls of the catheter lumens, the tips 112a, 114a, return to the pre-set curved position of FIG. 7. The straightened position is shown in phantom in FIGS. 6 and 7. The endoscopic instruments (tool), e.g. instruments 32, 34, follow the curve of the respective tool channel 112, 114 and the endoscopic tools 32, 34 are advanced out the distal openings 112d, 114d of the respective tool channels 112, 114 to expose the working end, e.g., the jaws, for performing the surgical procedure. Thus, since the tool channels 112, 114 have the double curve, the instruments 32, 34 need not have the double curve as they can take the shape of the tool channels 112, 114. However, alternatively, the instruments could also have the double curve shape like the tool channels 112, 114.

The tool channels 12, 14, 112, 114 can be composed of superelastic material, although other materials to provide the curved tip which returns from a substantially straight insertion shape to a curved shape when exposed can also be used, such as stainless steel. Also, as in the other embodiments disclosed herein, shape memory properties of material such as Nitinol can be used with a memorized curved tip shape. In alternative embodiments, the tool channels 12, 14, 112, 114 can have a mechanism such as a pull wire which is actuated to bend its distal end. The tool channels can be unattached to the catheter 11 so that the user can freely control their axial movement from a proximal end portion during use, the proximal end extending proximally of the proximal end of the catheter. However, it is also contemplated that in alternate embodiments the tool channels can be attached to the catheter. In the embodiments where the tool channel is not utilized and the instruments are inserted directly through the catheter lumens, e.g., FIG. 4D, or where the tool channels are of shorter length and terminate adjacent the opening of the catheter (adjacent the proximal end of the expanded region), e.g., FIG. 5C, the endoscopic instruments 130, 132 would have the single curve with a pre-bent distal tip curving toward the target tissue (like the pre-curve of tool channel 12) or have a double curve with a pre-bent distal tips having a first bend extending away from the target tissue and transitioning to a second bend extending downwardly toward the target tissue. In the embodiment with the single bend tool channels, e.g., tool channels, 12, 14, the endoscopic instrument can rely on the single bend of the tool channels 12, 14 to form the bend of the instruments or the instrument can also have the single bend. In the embodiment with the double bend tool channels, e.g., tool channels, 112, 114, the endoscopic instrument can rely on the double bend of the tool channels 112, 114 to form the bend of the instruments or the instrument can also have the double bend. The double bend of the tool channels and/or endoscopic instruments increases the distance from the target tissue as the instruments would first curve away from the target tissue and then bend toward the target tissue. Such increased distance improves maneuverability of the instruments and visibility. Note the single bend tool channels, the double bend tool channels, the short tool channels and no tool channels can be utilized with any of the embodiments disclosed herein The tool channels 12 and 14 (and 112, 114) can optionally include markings at a region proximal to the catheter 11 (or 61) to provide a visual indicator to the user of the depth of insertion of the tool channels 12, 14 (and 112, 114) through the catheter lumens 17, 19. The tool channels 12, 14 (and 112, 114) can have a luer fitting with a valve, at the proximal end which can close off backflow of insufflation gas from the body. This maintains insufflation when the endoscopic tool is inserted through the tool channels. The tool channels in an alternate embodiment can have a hemostatic valve connected at a proximal end to maintain insufflation during tool insertion.

The catheter 11 includes a handle (handle housing) 24 at the proximal portion 13. The handle can be any of a variety of shapes to provide a desired or ergonomic position for operation of the system. Catheter 11 also includes tubing 26 having a luer coupling and a control switch for closing off an internal gasket. Catheter 11 also has tubing 27 having a one-way stopcock to provide an insufflation port for providing gas insufflation into the body lumen. This port in some embodiments can be used to supplement the insufflation gas provided by the endoscope 30. The insufflation gas flows through lumen in the area around the endoscope 30 since the cross sectional dimension of the lumen exceeds the cross-sectional dimension of the endoscope 30 to leave a sufficient gap. Alternatively, tubing 26 can additionally or alternatively be used to inflate the expandable portion 40 of the catheter 11, or another port can be provided for injection of inflation fluid into fluid channel 42 within catheter 11 which communicates with the expandable member 40

A seal can be provided within the housing anywhere along the handle. Seals can be provided in the catheter lumens to limit gas leakage in the space between the outer wall of the tool channels 12, 14 and the inner wall of the respective lumens of the catheter. Similarly, a seal can be provided in the lumen for the endoscope to limit gas leakage in the space between the outer wall of the endoscope and the inner wall of the lumen. Such seals within the lumens can be located in a region within the handle. In some embodiments, the seal is in the form of a membrane with a central round hole, and in some embodiments located distally in the handle 24 for the endoscope and proximally in the handle for the tool channels. That is, for example, a membrane seal can be provided in the lumen for the endoscope, in the lumen for tool channel 12 and in the lumen for tool channel 16. Note other types of seals are also contemplated. Note in some embodiments the seals can also provide some resistance to axial movement of the endoscope and axial movement of the tool channels to help retain their axial position until a predetermined force is applied An external seal, such as a sponge-like cuff, balloon or other blocking device, can be provided such as cuff positioned around the catheter shaft, preferably at a proximal portion, to occlude the space, e.g., rectal space, between the catheter shaft and the body space wall, e.g., rectal wall, to minimize leakage.

Indicia can be provided on the flexible guides so the user can match the proximal end of the flexible guide with the distal end within the chamber formed by expandable member 40.

In one embodiment, the tool channels 12, 14 (and 112, 114) can be composed of a flexible soft material, such as Pebax. A superelastic nitinol backbone can in some embodiments be embedded in the wall of the Pebax material, e.g., within the curved portion. Other materials are also contemplated.

Catheter 11 also preferably has a lumen configured and dimensioned to receive an endoscope 30. In some embodiments, the lumen is dimensioned to receive a conventional endoscope, e.g., a conventional colonoscope, and the catheter 11 is backloaded over the endoscope. In alternate embodiments, the lumen can receive an articulating endoscope. Moreover, in alternate embodiments, the endoscope can be inserted into the catheter already inserted into the body lumen.

Figure 2A:
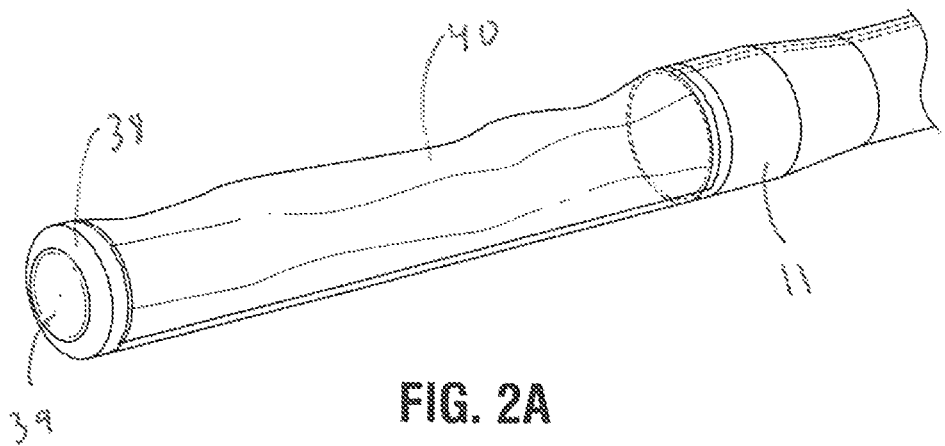
FIG. 2A is an enlarged perspective view of the distal portion of the catheter of FIG. 1 showing the balloon in the non-expanded position.
Figure 2B:
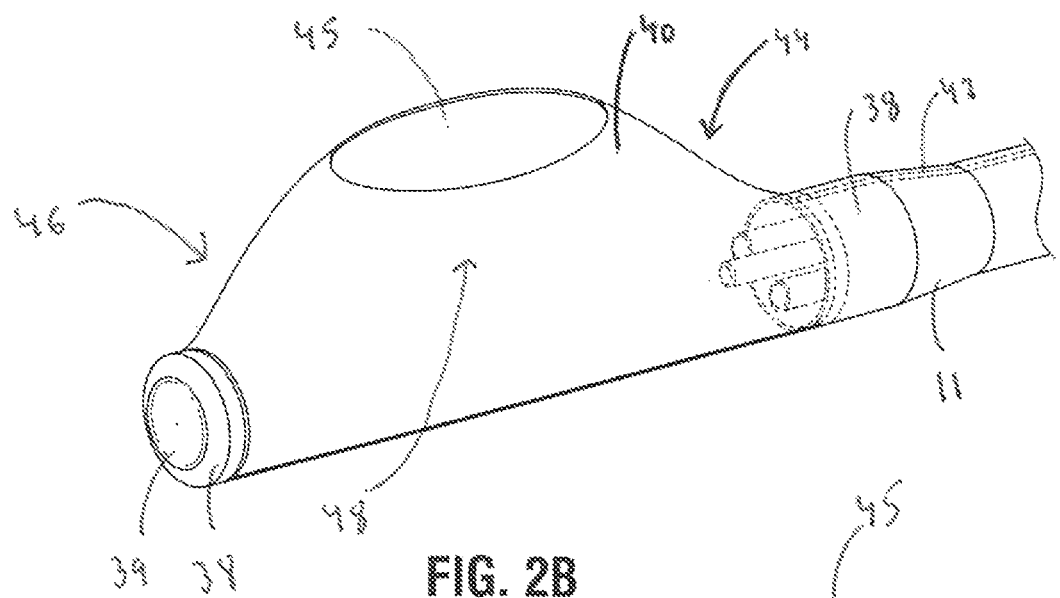
FIG. 2B is a perspective view similar to FIG. 2A showing the balloon in the expanded position.
Figure 3:
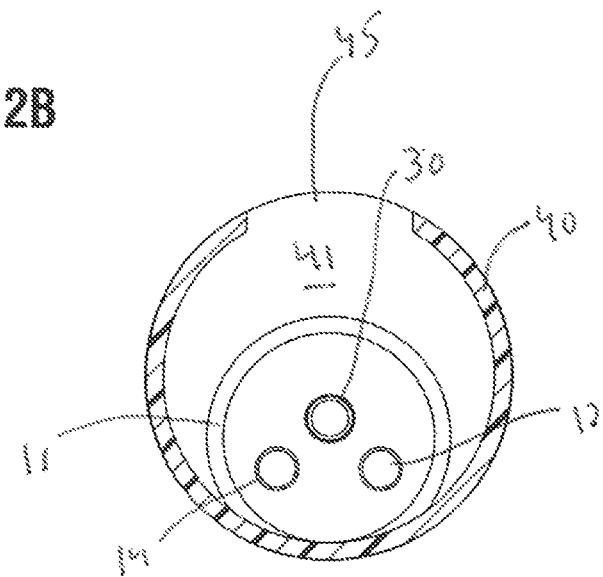
FIG. 3 is a cross-sectional view of a distal portion of the catheter of FIG. 1 showing the balloon in the expanded position.
Figure 4B:
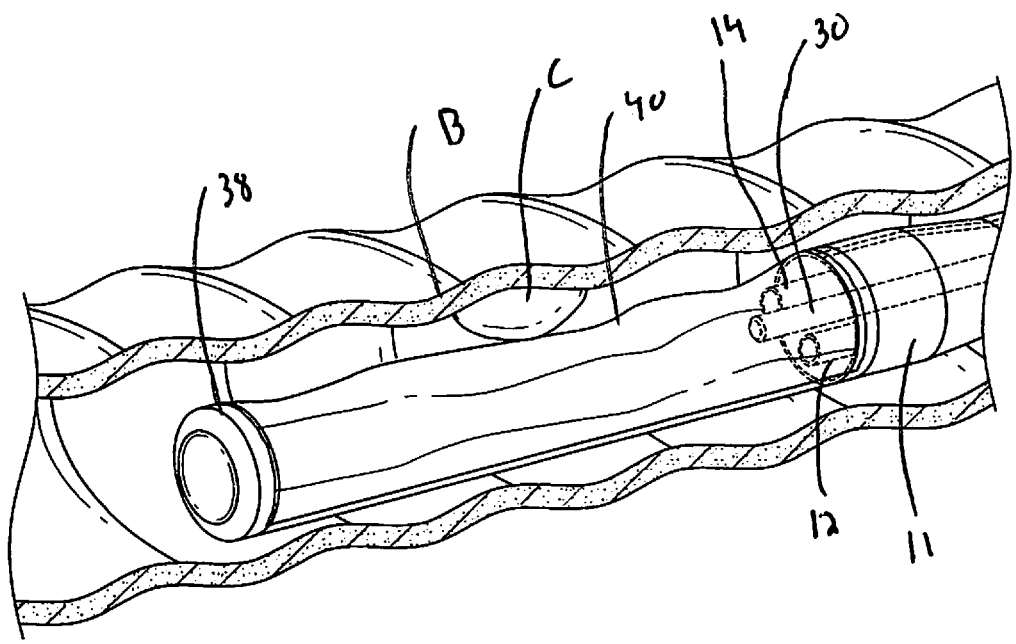
FIG. 4B is view similar to FIG. 4A showing further advancement of the catheter of FIG. 1 to position the balloon window adjacent the lesion.
Figure 4C:
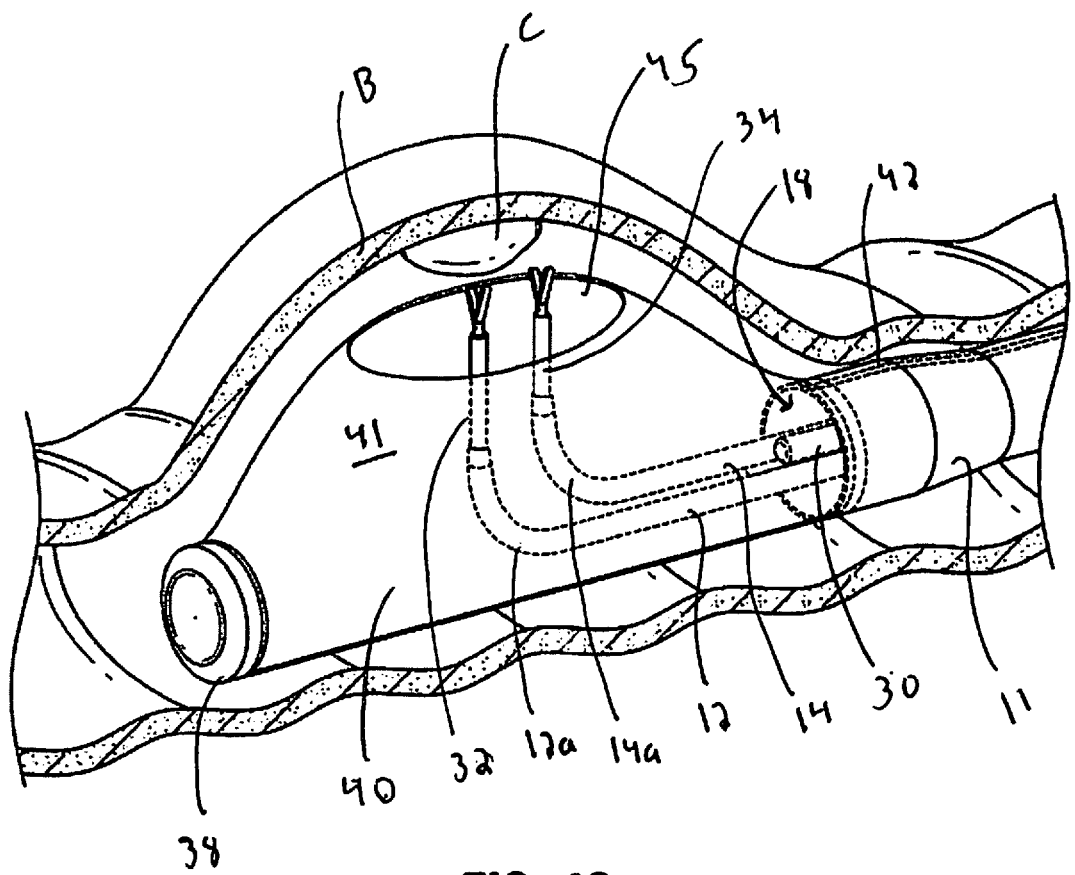
FIG. 4C is a view similar to FIG. 4B showing expansion of the balloon to provide an expanded chamber and further showing tool channels (instrument guides) and endoscopic tools (instruments) inserted through the instrument guides.
Figure 4D:
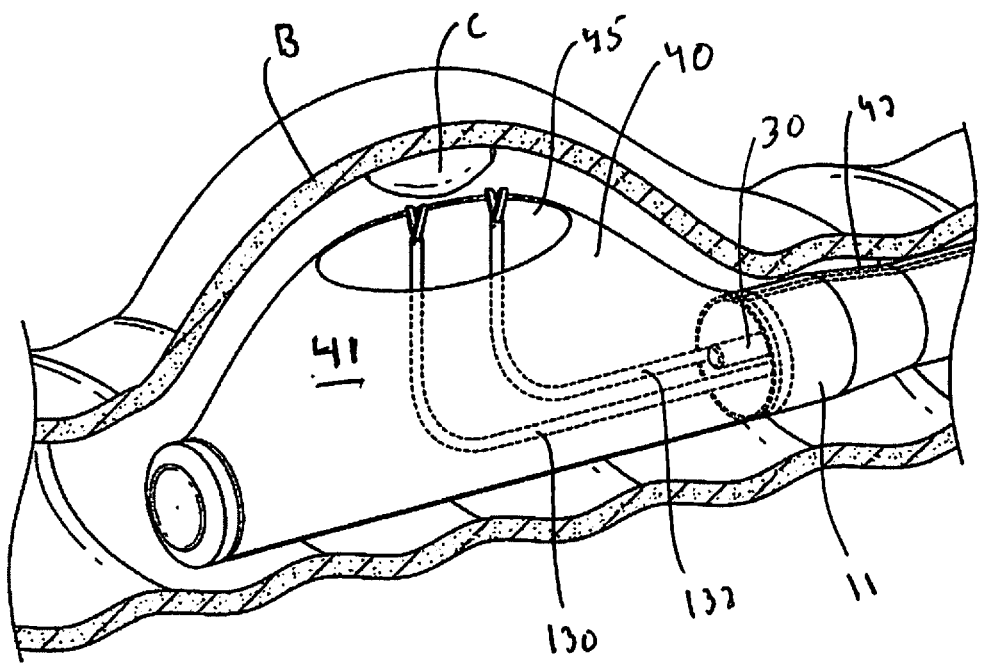
FIG. 4D is a view similar to FIG. 4C showing an alternate embodiment wherein the endoscopic tools are inserted through the catheter without the use of tool channels.

Expandable member or portion 40 at the distal portion of catheter 11 as shown has a reduced profile collapsed insertion position (condition or configuration) shown in FIGS. 1, 2A, and 4B, and is expandable to an expanded position (condition or configuration) of FIGS. 2B and 4C (and 4D) to expand and/or reshape the body lumen to create a chamber of increased transverse dimension. The expandable member 40 is expandable by injection of inflation fluid through channel 42 which communicates with expandable portion 40. When expanded, it moves the wall B of the body lumen A which has the target tissue, e.g., lesion C, to expand the wall B containing the lesion C to provide an increased working space, i.e., increased space between the catheter 11 and the window 42 of the expandable portion 40. Note in the embodiment of FIGS. 1-4D, the expandable member 40 is in the form of an inflatable balloon having a U-shape or C-shape in cross-section so that the interior of or space within the U (FIG. 3) creates an expanded working space 41 for the working instruments, e.g., provides space for the curves of the instruments. This enables the instruments 32, 34 or 130, 132 inserted into the space to have an increased distance from the lesion than would not otherwise be available in the absence of such expansion. Note that in a preferred embodiment, the expandable member 40 is expandable asymmetrically, i.e., to only one side of a longitudinal axis of the catheter 11, so that only the wall containing the target tissue is moved. In the embodiments of FIGS. 1-4D, the expandable member 40 has a proximal portion 44, a distal portion 46 and an intermediate portion 48. The intermediate portion 48 has a greater height (transverse dimension) than the proximal and distal portions 44, 46, forming an arcuate shape in an axial direction as shown. The window 45 is formed at the apex of the curve. In the embodiment of FIGS. 5A-5D, described in detail below, the expandable portion 40 has a more uniform transverse dimension along its axial length.

The expandable member 40 (retractor) is shown in the form of an expandable balloon attached to the catheter 11 at a proximal and distal portion by known techniques for asymmetric expansion of the working space.

Window 45 formed in the expandable portion 40 due to its U-shape provides access to the target lesion. The window 42 is shown axially aligned with expandable member 40. The window 45 can be of various shapes and sizes other than that shown, provided it is a large enough opening for the endoscopic instruments to access and treat the target tissue, e.g., a lesion on the wall of the body lumen, on the wall which is expanded by the expandable member 40. In some embodiments, the window can be dimensioned to enable polyps or other removed tissue to be placed inside the expanded region for encapsulation and withdrawal when the expanded region is collapsed and the catheter 11 withdrawn from the body.

The catheter 11 can include a distal cap 38 having a membrane or a balloon like material 39 forming a seal. The endoscope 30 can be inserted through the seal 39 as shown in FIG. 4A to view the region distally of the catheter 11 during insertion. The endoscope 11 can then be retracted proximally with the seal resealing. The seal 39 restricts or occludes air flow as well as other fluid flow. Such seal can be used in any of the embodiments disclosed herein.

The use of the system 10 of FIG. 1 will now be described with reference to removing a lesion, such as a polyp, from a colon wall, it being understood, however, that the system 10 can used for other procedures within the colon or the gastrointestinal tract, as well as used for other procedures in other body lumens or body spaces of a patient.

Turning first to FIG. 4A, a distal viewing endo scope 30, in which the catheter 11 has been advanced over the proximal end thereof, or alternatively the catheter 11 has been backloaded over the distal end thereof, is inserted through lumen A in the colon in a procedure to remove the target polyp C from the wall B of the colon. The endoscope 30 in this embodiment is a distal viewing scope with a wide distal viewing area of, for example about 150-170 degree range, so the polyp C and surrounding area can be visualized. The endoscope 30 is positioned so the viewing lens (and illumination) at the distal end 30a extends through the seal 39, e.g., membrane 39 of distal cap 38 of catheter 11, for forward viewing distally of catheter 11, with the membrane 39 maintaining the seal. After placement of the endoscope 30 adjacent the target tissue, i.e., slightly proximal of the target polyp C, the catheter 11 is further advanced over the endoscope 30 to the position of FIG. 4A. The catheter 11 is advanced over the endoscope 30 as shown in FIG. 4B until the window (opening) 45 of expandable member 40 is aligned with the polyp C. As can be appreciated, in this insertion position of the catheter 11, the expandable member 40 is in the non-expanded (or collapsed) position. As shown, in this position, the distal end 30a of the endoscope 30 is preferably positioned at the end of distal opening 18 of catheter 11, i.e., proximal of the window 42, so as not to extend into the working space 41 created by the expandable member 40 to thereby leave more room for maneuvering of the tool channels and/or endoscopic instruments within the working space. Other positions, however, are also contemplated, e.g., in some versions the endoscope 30 can extend into the working space 41 created by the expandable member 40.

Next, the expandable member 40 is expanded, e.g., by injection of inflation fluid through channel 42, as shown in FIG. 4C, thereby creating the asymmetric working space (chamber) 41 in the interior of the balloon and any gap (space) between the expandable member and wall. Thus, the expandable member 40 expands the chamber to one side of the longitudinal axis of the catheter and retracts tissue by the target tissue e.g., lesion.

Next, tool channels 12, 14 are inserted through the ports in the proximal region of the catheter 11 and advanced by the user through the catheter lumens so they extend out the distal openings of the lumens and into the expanded working space (expanded chamber) 41 as shown in FIG. 4C. As the tool channels 12, 14 emerge from the lumens of the catheter 11, and out of the confines of the lumen walls of the catheter 11, their distal tips 12a, 14a return to their curved (pre-bent) position, curving upwardly (as viewed in the orientation of FIG. 4C) toward the polyp C. In the embodiment utilizing tool channels 112, 114, as the tool channels emerge from the lumens of the catheter 11, and out of the confines of the lumen walls of the catheter 11, their distal tips 112a, 114a return to their curved (pre-bent) position, curving downwardly away from polyp C and then curving upwardly toward polyp C. Note the terms upwardly and downwardly as used herein refer to the orientation of the system in the referenced Figures—if the position of the system changes, the orientation and terms would also change. Note the tool channels 12, 14, 112, 114 can be independently rotated and/or moved axially to adjust their position with respect to the polyp C. Note in the alternate embodiment of FIG. 5C, the tool channels 212, 214 extend slightly distally of the distal opening 18 of the catheter 11 terminating proximal of window 142 (or alternatively terminating at a proximal region of the window 42) and need not be provided with the curved distal end. In his embodiment of FIG. 5C, the instruments would have curved tips to access the target tissue. Further note that in the embodiment of FIG. 4D where tool channels are not provided, this step of insertion of the tool channels is skipped and the endoscopic instruments 130, 132 are inserted directly through the catheter 11. The instruments 130, 132 have curved distal ends as shown. Note in FIG. 4C, the expandable member 40 is first expanded, followed by insertion of the tool channels 12, 14 out of the catheter lumens and into the working space 41. However, it is also contemplated that in an alternative embodiment, the tool channels 12, 14 can be inserted through the catheter lumens 17, 19 prior to expansion of the expandable member 40.

After insertion of the tool channels 12, 14 (or 112, 114), endoscopic instruments (tools) 32, 34 (or 130, 132) are inserted through the luer fitting of the tool channels 12, 14 (or 112, 114) and advanced through the lumen (channel) of the tool channel. As shown in FIG. 4C, a first endoscopic instrument 32 extends from tool channel 12 and out the distal opening 12b into the expanded working space 41 created by the expandable member 40. Similarly, a second endoscopic instrument 34 extends from tool channel 14 and out the distal opening 14b into the expanded working space 41 created by the expandable member 40. The endoscopic instruments 32, 34 follow the curved shape of the tool channels, extending toward the polyp C when exposed from the tool channels. As noted above, the tool channels can include a valve (26, 28), such as hemostatic valves, so insufflation is not lost during insertion and removal of the endoscopic instruments from the tool channels. The endoscopic instruments therefore extend laterally with respect to a longitudinal axis of the catheter to contact and treat tissue, e.g., remove the polyp C. As can be appreciated, once the tool channels 12, 14 (or 112, 114) are in the desired position with respect to the polyp C, they can be considered as defining a fixed curve. This means that when the endoscopic instruments are axially advanced, they move closer to the target polyp C, without a change in curvature and without a change in their axial position with respect to the polyp C, thus providing an extra degree of freedom. In some embodiments, one endoscopic instrument can be a grasper to apply tension on the polyp C while another endoscopic instrument can be an electrosurgical dissector to dissect/sever the polyp C from the colon wall B. Other endoscopic instruments for polyp removal can also be utilized. Additionally, in some embodiments, a single tool channel can be utilized and another endoscopic instrument, e.g., a grasper or a dissector, can be inserted through a working channel (lumen) of the endoscope. Such instrumentation inserted through an endoscope can also be utilized with the embodiments having two or more tool channels. Also note that due to the angles of the endoscopic instruments, the instrumental triangulation can be achieved.

After removal of the polyp C from the colon wall B, it can be placed within the catheter 11 for removal from the body. Expandable member 40 is deflated to return the expandable member 40 to its collapsed position of FIG. 4B for removal of the catheter 11.

In some embodiments, the removed polyp or other structure is placed within the space within the expandable member 40 and the expandable member is deflated (collapsed) to close or substantially decrease in size the window 45 and encapsulate the removed tissue for removal from the body lumen.

FIGS. 5A-5D show an alternate embodiment of an expandable region or portion for increasing the working space. In the embodiment of FIGS. 5A-5D, the system 60 is identical to system 10 of FIG. 1 except for the expandable portion (member). More specifically, flexible catheter 61 of system 60 is identical to flexible catheter 11 except that the expandable member 62 is elongated and of substantially the same cross-sectional (transverse) dimension along its length, thereby forming a substantially cylindrical shaped expandable portion. Expandable portion 62 is in the form of an expandable balloon with an inflation lumen 65 extending through the catheter 61 and communicating with the expandable member (balloon) 62. Being otherwise identical, for brevity, other features of the catheter 61 and system 60 are not discussed herein since the features and function of system 10 and catheter 11 are fully applicable to system 60 and catheter 61. Additionally, the various embodiments of the tool channels discussed above, e.g., short tool channels such as tool channels 212, 214, single curved tool channels such as tool channels 12, 14, and double curved tool channels such as tool channels 112, 114, can be utilized with system 60. Alternatively, the endoscopic instruments can be inserted through catheter 61 without tool channels as in the embodiment of FIG. 5D (and the aforedescribed embodiment of FIG. 4D). The endoscopic instruments discussed above, e.g., double curved instruments or instruments 130, 132 can be utilized with the system 60. By way of example, system 60 is shown with tool channels 212, 214 terminating adjacent distal opening 63 and endoscopic instruments 130, 132 extending therefrom.

Figure 5A:
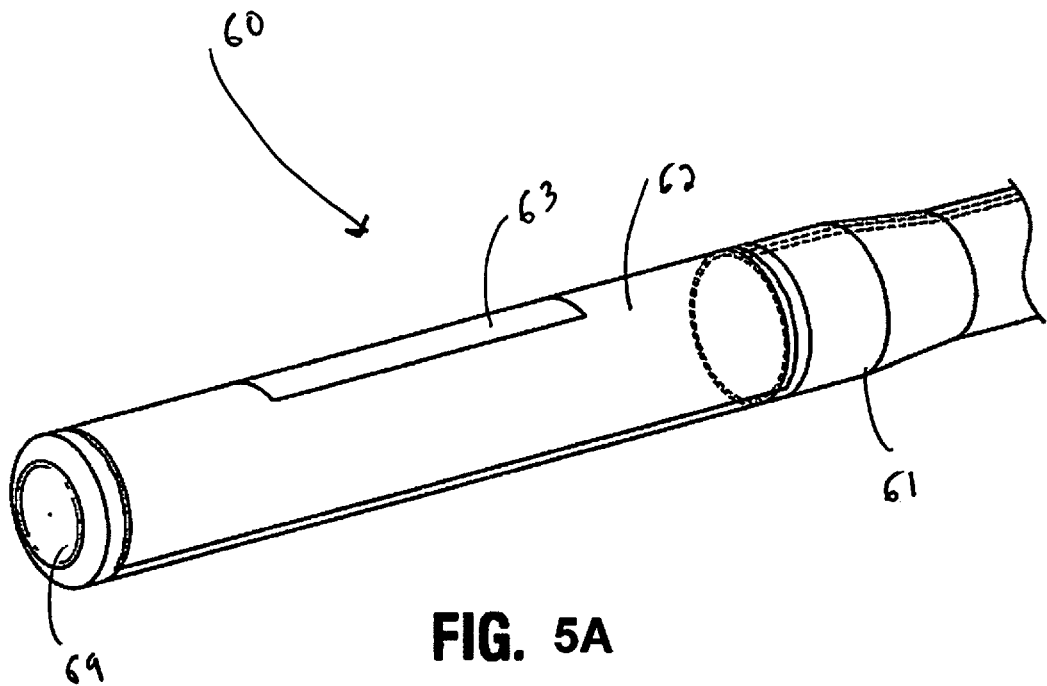
FIG. 5A is a perspective view showing the distal portion of the catheter of an alternate embodiment with the balloon in the non-expanded position.
Figure 5B:
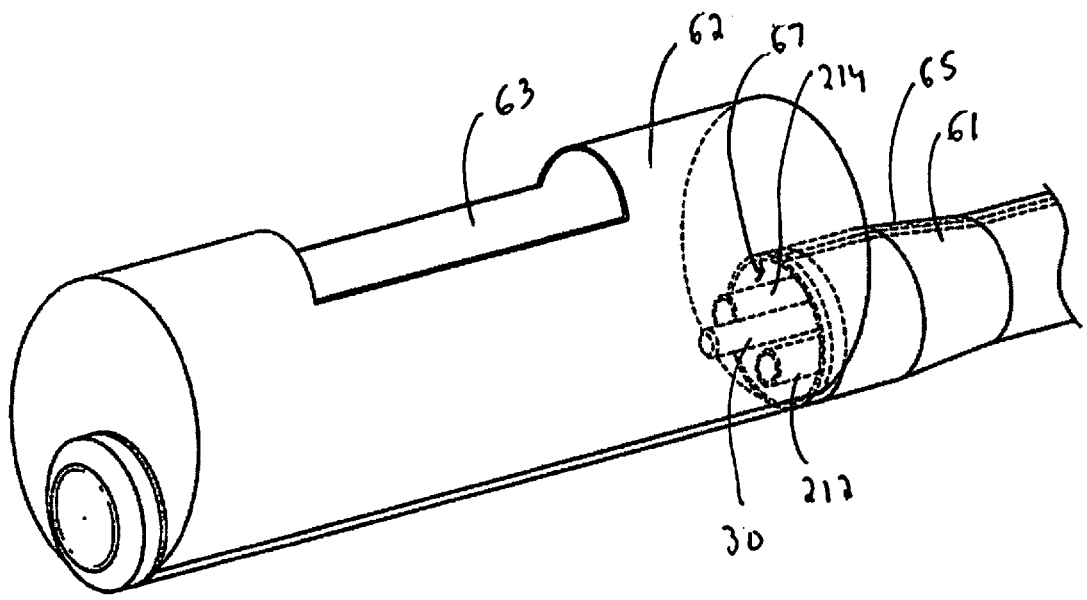
FIG. 5B is a perspective view similar to FIG. 5A showing the balloon in the expanded position.

Note the catheter 61, like catheter 11, can have a seal 69 like seal 39 of FIG. 1, which minimizes the space/gap between the endoscope 30 and the distal cap (hence, minimizing fluid leak around the endoscope 30 and the chance of the tissue entrapment in the gap) while permitting an advancement of the endoscope 30 therethrough for viewing distally of the catheter and then retracted to the position of FIG. 5B for viewing of the expanded region of the endoscopic instruments. The endoscope 30 can be inserted through catheter lumen 72 in the same manner as in the FIG. 1 embodiment.

Inflation of expandable member 62 creates an increased working space of increased transverse dimension for manipulation of endoscopic instruments, e.g., instruments 130, 132 inserted through the catheter 61 (and exiting distal opening 67), within the increased working space. This asymmetric expansion, e.g., expansion to only one side of a central longitudinal axis of the catheter 61, causes radial outward bulging to increase the working space adjacent the target tissue.

After the procedure, e.g., removal of a polyp via access of instruments 130, 132 through window 63 positioned in the expanded member 62 adjacent the polyp, the polyp C or other removed tissue structure from the colon wall B can be placed within the space within the expandable member 62 and the expandable member 62 can be deflated (collapsed) to close the window 63 and encapsulate the removed structure for removal from the body lumen. The window 63 can be of various shapes and sizes other than that shown, provided it is a large enough opening for the endoscopic instruments to access and treat the target tissue, e.g., a lesion on the wall of the body lumen, on the wall which is expanded by the expandable member 62.

In some embodiments, it may be advantageous to provide for articulation of the distal portion of the catheter, before expansion and/or after expansion. Various mechanisms to effect articulation can be utilized, such as elongated members embedded in the catheter wall on opposite sides of the catheter. The articulation members can be in the form of elongated wires, or alternatively in the form of other elongated members such as cables or tubes. To articulate the distal portion of catheter in a first direction, one of the articulation members is pulled proximally; to articulate the distal portion of catheter in a second opposite direction, the other articulation member is pulled proximally. Movement of the articulation members back to their original position returns the catheter to the non-articulated straighter position. Such articulation improves the positioning of the expandable region of the system.

The expandable portion can in certain embodiments be closable for insertion and removal.

In alternative embodiments of the system of the present invention, the system can include floating (flexible) channels within the catheter. In one embodiment, the floating channels are fixed at their proximal and distal ends; in another embodiment the floating channels are fixed at their proximal ends but are unattached at their distal ends. The floating channels reduce the overall stiffness of the catheter (outer tube) which would otherwise be stiffer if the channels were fixed along their entire length and did not float within the catheter. The floating channels also reduce kinking of the tool channels (flexible guides) inserted through the floating channels and reduce kinking of the tools inserted through the tool channels (or inserted directly through the floating channels in the embodiments where the tool channels are not utilized). Floating channels which can be utilized are disclosed in application Ser. No. 14/622,831, (Publication no. 2015/0157192) filed Feb. 14, 2015, the entire contents of which are incorporated herein by reference.

The catheter in some embodiments can have a single lumen dimensioned to receive 1) an endoscope; and 2) two flexible channels in the form of flexible tubes that float inside the lumen. That is, the two floating channels have intermediate portions that can move radially (laterally) within the lumen of the catheter. Stated another way, the floating channels are unconstrained within the catheter so they can bend relative to the catheter so their bending action does not need to follow that of the catheter. In this manner, when the catheter is inserted in the body lumen and needs to bend to accommodate the curvatures of the body lumen, e.g., the gastrointestinal tract, the flexibility of the catheter is maintained since the floating channels can move within the lumen of the catheter, thereby increased flexibility is achieved. It should be understood that any of the systems disclosed herein could be provided with floating channels. Likewise, any of the systems disclosed herein could be provided without floating channels. The tool channels disclosed herein can be inserted through the floating channels or alternatively the endoscopic instruments can be inserted directly into the floating channels. Also, by providing a single lumen to receive the endoscope and the tool channels, rather than separate lumens which would require additional wall structure, a smaller diameter catheter can be provided which also reduces the overall stiffness of the catheter. The endoscope, e.g., endoscope 30, can in some embodiments also float within the lumen. That is, the endoscope can occupy only a certain region of the lumen and can move radially (laterally) within the lumen of catheter to increase the flexibility of the system. Thus, the endoscope can move relative to the catheter in a similar manner as the floating channels can move relative to the catheter.

The working instruments can include graspers or dissectors for example. A dissecting/cutting instrument or a grasper can be inserted through the flexible guide in the floating channel, or alternatively inserted through a working channel of the endoscope. Thus, various working instruments can be inserted through the flexible guides and endoscope channel(s).

The expandable members disclosed herein form a retractor system that when expanded from its collapsed insertion position forms a working space expanding system and in certain surgical procedures a body lumen reshaping system which reshapes the body lumen to form an asymmetric space without stretching the body lumen wall beyond a point when it can be injured, e.g., lacerated by the stretching force, to increase the working space for the maneuverability of the endoscopic instruments. That is, the retractor system forms an expanded area within the body lumen for the surgeon to perform the surgical procedure. By reshaping the body lumen, the working space is maximized without overstretching the body lumen. Such working space maximization increases the distance between the target tissue and the end effectors (working tips) of the endoscopic instruments, hence improving maneuverability of the instruments during the surgical procedure. In such reconfiguring, the body lumen shape can be changed from a substantially circular cross-sectional configuration to a somewhat oval shape configuration where the walls are elongated. Thus, the expandable member changes the colon shape at the desired site to a narrower width, thereby reconfiguring the colon lumen, to increase working space for the instruments.

The expandable members of the embodiments disclosed herein can in some embodiments stabilize the luminal wall motion which may be more prominent in the gastrointestinal tract. This may facilitate the surgical procedure, particularly in the gastrointestinal tract.

The expandable members of the embodiments disclosed herein can also provide a seal within the body lumen as they fill the space within the body lumen.

In use, the instruments can access tissue protruding through the window into the chamber and/or can protrude through the window to access tissue outside the window.

Note that the various embodiments of the catheter described above are expandable to alter the working space within the body space or body lumen. As the working space is expanded, the distance between the instruments and the target tissue is increased, hence, facilitating the instruments' maneuverability and ability to perform more advanced surgical techniques inside the lumen, e.g., tissue retraction, dissection, repair. As the expandable member expands, it may press on and deflect at least a portion of the luminal wall. As a result, the shape of the lumen can be changed depending on the size and shape of the expandable member, the extent of its expansion and the size and shape of the body lumen. In smaller diameter body lumens, such as the bowel, the expansion of the expandable member may substantially reshape the body lumen as described above. This reshaping can also occur in larger diameter body lumens. However, it should also be appreciated that in certain larger diameter body lumens, such as the stomach, and especially when insufflation is utilized for the surgical procedure, the body lumen may not necessarily be reshaped. However, even in this case, the expanded member (region) applies a radial force against the body wall to alter the working space. Therefore, whether the catheter is used in small or larger diameter working spaces/lumens, it advantageously moves the wall to increase the distance between the tips of the instruments and the target tissue, thereby functioning as a working space expanding system to facilitate access and maneuverability as described in detail above. As can also be appreciated, the dynamic nature of the expandable region with its controlled expansion enables the system to function as an organizer to adjust and optimize the distance between the tips of the instruments and the target tissue. Also note that in larger diameter body lumens, a symmetric chamber might also be able to be utilized, although not optimal.

Note the endoscopic instruments can be used for partial tissue resection, for example, submucosal or subserosal resection. The endoscopic instruments could also be utilized for full thickness tissue resection. The instruments enable removal of the lesion with healthy tissue margins, thereby providing a complete, en-block removal of the pathological lesion.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

What is claimed:

1. A system for endoscopic surgery within a body lumen of a patient comprising:
   a flexible catheter having a proximal portion, a distal portion, and an expandable balloon at the distal portion,
   the expandable balloon having a side access opening,
   the expandable balloon inflatable to expand from a collapsed configuration to an expanded configuration, and having an increased transverse dimension to provide an expanded chamber on a first side of the catheter,
   the side access opening positioned on a first side of the expandable balloon, wherein the side access opening is sized to allow removal of target tissue through the access opening,
   the catheter including a lumen dimensioned to receive an endoscopic instrument therethrough such that a distal end of the endoscopic instrument is positionable within the expanded chamber and angleable laterally within the expanded chamber to engage and remove the target tissue through the side access opening,
   the lumen of the catheter having an opening at a distal end thereof communicating with the expanded chamber,
   the catheter further dimensioned to receive a visualization device to visualize the endoscopic instrument while removing the target tissue,
   wherein the endoscopic instrument is movable independently of the visualization device, and
   wherein when the expandable balloon is deflated from the expanded configuration to the collapsed configuration the side access opening is closed in order to be configured in encapsulating the removed target tissue from the body lumen via removal of the catheter from the body lumen.

2. The system of claim 1, wherein the catheter includes an inflation channel for expanding the balloon.

3. The system of claim 2, wherein the expandable balloon is C-shaped in transverse cross-section.

4. The system of claim 1, wherein the expandable balloon is generally uniform in transverse dimension along its length.

5. The system of claim 1, further comprising an articulation member for angling the distal portion of the catheter with respect to a longitudinal axis of the catheter.

6. The system of claim 1, wherein the expandable balloon has a U-shape forming a space within the U.

7. The system of claim 1, wherein the endoscopic instrument has a first curve extending in a first direction and a second curve extending in an opposite direction, the first curve angling away from the access opening and the second curve angling toward the access opening.

8. The system of claim 1, wherein the catheter has a seal at a distal end thereof and the visualization device is movable through the seal to visualize distally of the catheter.

9. The system of claim 1, wherein an intermediate portion of the expandable balloon has a transverse dimension greater than a proximal and distal portion of the expandable balloon, and the side access opening is located in the intermediate portion.

10. The system of claim 9, wherein the intermediate portion has an arcuate shape in an axial direction.

11. The system of claim 10, wherein the side access opening is positioned at an apex of the arcuate shape.

12. The system of claim 1, further comprising an articulating endoscope insertable through a channel of the catheter.

13. The system of claim 1, further comprising an endoscope receiveable within the lumen of the catheter, wherein the catheter is backloadable over the endoscope.

14. The system of claim 1, further comprising an endoscope insertable into the catheter after the catheter has been inserted into the body lumen.

15. The system of claim 1, wherein the side access opening is sized and configured so that when the expandable balloon is in the expanded configuration, tissue protruding through the side access opening into the expanded chamber is accessible by the endoscopic instrument.

16. The system of claim 1, wherein the side access opening is sized and configured so that when the expandable balloon is in the expanded configuration, the endoscopic instrument is extendable through the side access opening to access tissue disposed outside the expanded chamber.

* * * * *